United States Patent [19]

Cortes et al.

[11] Patent Number: 4,935,145

[45] Date of Patent: Jun. 19, 1990

[54] ON-LINE COUPLED LIQUID AND GAS CHROMATOGRAPHY SYSTEM

[75] Inventors: Hernan J. Cortes; Curtis D. Pfeiffer, both of Midland, Mich.; Bruce E. Richter, Sandy, Utah

[73] Assignee: The Dow Chemical Company, Midland, Mich.

[21] Appl. No.: 348,240

[22] Filed: May 5, 1989

Related U.S. Application Data

[63] Continuation-in-part of Ser. No. 209,609, Jun. 21, 1988, abandoned, which is a continuation of Ser. No. 902,911, Aug. 26, 1986, abandoned, which is a continuation of Ser. No. 810,798, Dec. 8, 1985, abandoned, which is a continuation-in-part of Ser. No. 695,038, Jan. 18, 1985, abandoned.

[51] Int. Cl.$^5$ .............................. B01D 15/08
[52] U.S. Cl. ................................ 210/656; 55/67; 55/386; 210/198.2; 436/161
[58] Field of Search ............... 210/656, 198.2, 635; 55/67, 197, 386; 436/161; 422/70

[56] References Cited

U.S. PATENT DOCUMENTS

| | | | |
|---|---|---|---|
| 3,507,147 | 4/1970 | Llewllym | 55/386 |
| 4,274,967 | 6/1981 | Snyder | 55/386 |
| 4,383,839 | 5/1983 | Sisti et al. | 55/67 |
| 4,470,832 | 9/1984 | Sugawara | 55/386 |
| 4,577,492 | 3/1986 | Holba | 422/70 |

OTHER PUBLICATIONS

K. Grob, Jr. et al., "Coupling of High-Performance Liquid Chromatography with Capillary Gas Chromatography," J. of Chromatography, 295 (1984).

K. Grob, Jr., "Band Broadening in Space" and the 'Retention Gap' in Capillary Gas Chromatography, J. of Chromatography, 237 (1982), 15–23.

K. Grob, Jr. et al., "Some Technical Aspects of the Preparation of a 'Retention Gap' in Capillary Gas Chromatography," J. of Chromatography, 244 (1982), 185–196.

Hernan Cortes et al., "Determination of Trace Chlorinated Benzenes in Fuel Oil by On-Line Multidimensional Chromatography Using Packed-Capillary Liquid Chromatography and Capillary Gas Chromatography," J. of Chromatography, 349 (1985), 55–61.

H. J. Cortes et al., "On-Line Multidimensional Chromatography Using Packed Capillary Liquid Chromatography and Capillary Gas Chromatography," J. of High Resolution Chromatography & Chromatography Communications, (1985), vol. 8, 469–474.

Hernan J. Cortes et al., "On-Line Multidimensional Chromatography Using Micro HPLC and Capillary GC," Chromatography Forum, Nov.–Dec. (1986), 29–34.

Ronald E. Majors, "Multidimensional High Performance Liquid Chromatography," J. of Chromatography Science, 18 (1980), 571–579.

J. A. Apffel et al., "Hydrocarbon Group-Type Analyses by On-Line Multi-Dimensional Chromatography," J. of Chromatography, 279 (1983), 139–144.

Primary Examiner—Ernest G. Therkorn
Attorney, Agent, or Firm—Burke M. Halldorson

[57] ABSTRACT

Apparatus and method for on-line coupled liquid chromatography and gas chromatography analysis includes a retention gap which allows injection of a substantial volume of sample-carrying eluent and concentrates bands, obviating adverse effects on the resolution or peak shape of the components of interest. The retention gap is used to simultaneously receive and vaporize liquid solvent in a manner highly suitable for purposes of gas chromatographically separating solutes of interest dispersed in the liquid chromatography solvent.

6 Claims, 5 Drawing Sheets

ON-LINE COUPLED LIQUID AND GAS CHROMATOGRAPHY SYSTEM

CROSS-REFERENCE TO RELATED APPLICATION

This application is a continuation-in-part of now abandoned application Ser. No. 209,609, filed June 21, 1988, which is a continuation of now abandoned application Ser. No. 902,911, filed Aug. 26, 1986, which is a continuation of now abandoned application Ser. No. 810,798, filed Dec. 18, 1986, which is a continuation-in-part of now abandoned application Ser. No. 695,038, filed Jan. 25, 1985.

BACKGROUND OF THE INVENTION

The present invention relates to high-performance liquid chromatography (HPLC) coupled directly with capillary gas chromatography (GC). More particularly, the invention is directed to a method and apparatus for on-line coupling of liquid and gas chromatography columns in which there is direct quantitative transfer of sample from a liquid chromatography analytical column to a gas chromatography column.

The transfer of a selected fraction from a liquid chromatograph into a gas chromatograph has been reported; however, analyses were performed either off-line, requiring collection and re-injection of the separate fraction (e.g., F. DeSanzo, et al., Anal. Chem. 52 (1980) 906), or on-line, using conventional high performance liquid chromatography columns, whereby only a fraction of the separated peak (nonquantitative analysis) or a well resolved component (limited quantitative analysis) could be transferred into a gas chromatograph (e.g., J. Apffel, H. McNair, J. Chromatogr. 279 (1983) 139: K. Grob, Jr., et al., J. Chromatogr. 285 (1984) 55).

Apffel and McNair used an ordinary GC autosampler as an interface between an HPLC detector and the gas chromatograph. The effluent from the HPLC column was routed through the syringe of the autosampler to waste. The liquid flowing through the syringe was analyzed by the injection of a few microliters into a vaporizing injector. This technique did not provide a direct LC-GC coupling as desired, however, due to the very small amount of liquid that could be successfully introduced into the GC system.

K. Grob, Jr., et al. employed a "retention gap" (typically an inlet having low or negligible retention compared to the gas chromatography stationary phase) in an on-column injection mode to transfer large volumes of liquid directly from an HPLC column to a GC column. However, no suggestion is given in this reference of simultaneously vaporizing the solvent (liquid chromatography mobile phase) as it is being transferred into the retention gap. In contrast, the teaching requires the formation of a flooded zone (30–100 meters) of liquid in the retention gap. Additionally, in all of the specific examples, precise temperature control insures that the retention gap is maintained at a temperature below the boiling point of the solvent until the solvent peak has passed through the GC column.

BRIEF SUMMARY OF THE INVENTION

A first aspect of the invention resides in the use of a retention gap to simultaneously receive and vaporize liquid solvent in a manner highly suitable for purposes of gas chromatographically separating solutes of interest dispersed in the solvent. Another aspect of the invention resides in a method and apparatus for injecting large volumes of liquid into a gas chromatography capillary column which lends to the practicality of on-line coupled LC-GC analysis. Still another aspect of the invention resides in the use of a low flow rate liquid chromatography column coupled to quantitatively transfer entire portions of sample diluted in eluent directly from the liquid chromatography column to a capillary gas chromatography column.

BRIEF DESCRIPTION OF THE DRAWINGS

Yet further objectives, aspects and advantages of the invention will in part be pointed out and in part apparent from the following detailed description considered together with the Drawings wherein.

DETAILED DESCRIPTION OF THE INVENTION

The present invention pertains to an on-line multidimensional system in which a highly efficient, preferably packed liquid chromatography capillary column is coupled to a capillary gas chromatography column. It is a very important feature of the invention that a high volume vaporizing chamber or conduit, or interface capillary tube, e.g., an uncoated fused silica tube 2–20 meters long and having an inner diameter of up to about 1 mm, is interposed mechanically between the output from the packed liquid capillary column and the input to the capillary gas chromatographic column, preferably a wall-coated open tubular type. The vaporizing chamber is an element which is also known as a "retention gap." An important aspect of the invention resides in the new use of a retention gap to simultaneously receive and vaporize liquid solvent in a manner highly suitable for purposes of gas chromatographing solutes of interest dispersed in the solvent.

The preferred combination of the invention which includes a packed capillary liquid chromatographic column in conjunction with the retention gap makes it feasible to utilize relatively small volumes of eluent. In other embodiments of the invention the liquid chromatographic column may be, for example, of the wall-coated, open tubular type.

Another important feature of the apparatus and method of the invention is the use of a switching valve to transfer liquid to the retention gap to effect an enhanced, practical and direct transfer of liquid from the liquid chromatography column to the gas chromatography column. A related feature of the method of the invention is that the retention gap or interface capillary tube and the gas chromatography column are enclosed in an oven or heating device, the temperature of which is controllable to effect a sequential traverse or vaporization, first of the eluent and then of the species of interest into the gas chromatography column.

DESCRIPTION OF PREFERRED EMBODIMENTS

The aim and objects of the invention are accomplished by providing an on-line coupled HPLC system and a gas chromatographic system employing a preferred packed capillary liquid chromatographic column in conjunction with a liquid vaporizing chamber or interface capillary tube or retention gap. The packed capillary liquid chromatographic column permits use of small volumes of eluent and of reduced flow rates. The liquid vaporizing chamber or conduit or retention gap allows the injection of a substantial volume of sample-carrying eluent and concentrates the bands of the species of interest obviating adverse effects on the resolution or peak shape of the components of interest. The vaporizing conduit is interposed between the packed capillary liquid chromatography column and the capillary gas chromatography column.

Figure 1:
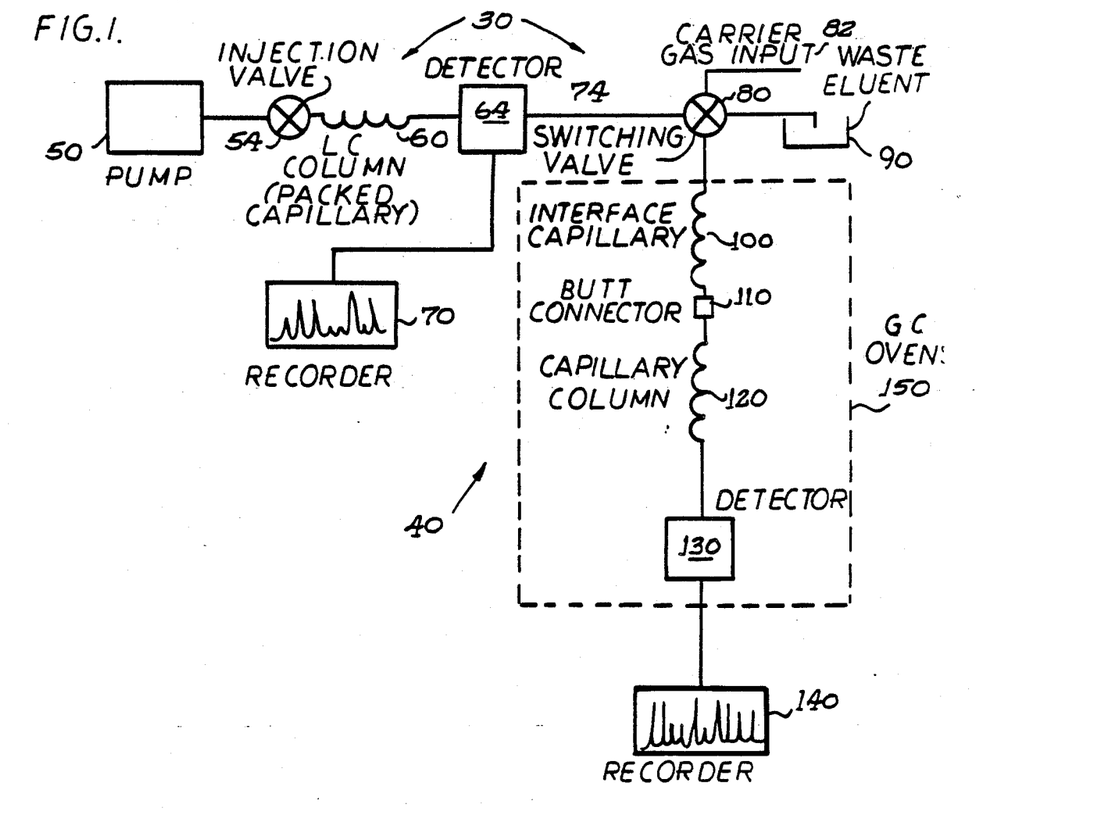
FIG. 1 is a schematic representation of an embodiment of apparatus of the invention.

Referring now briefly to the drawings, and particularly to FIG. 1, there is shown for illustrative purposes and not in any limiting sense a block diagram indicating schematically the various component elements of the apparatus of the invention. As shown, the chromatography system 20 includes a liquid chromatography section 30 and a gas chromatography section 40. The liquid chromatography section 30 includes a pump 50 connected through a sample injection valve 54 to a packed capillary liquid chromatography column 60. The effluent from the column 60 is connected to a detector 64 which is connected in turn to recording apparatus 70. The detector 64 is connected through a suitable conduit 74 to a switching valve 80 from which an aliquot of the effluent from the detector is directed to the gas chromatography system 40, through which switching valve, a carrier stream 82 is also introduced into the system. A suitable line 84 is provided to direct excess effluent to waste 90.

Referring now to the gas chromatography section 40, there is indicated, schematically, an interface capillary tube, or vaporizing chamber or retention gap 100 which receives the sample aliquot from the switching valve 80. The interface capillary gap or vaporizing chamber or retention gap 100 is connected by means of a "butt" connector 110 to a gas chromatography capillary column 120, the latter being connected to a detector 130, and the detector to a recorder 140. With the exception of the recorder 140, the components of the gas chromatography system are housed within a temperature controlling oven 150.

The method of the invention, described briefly with reference to FIG. 1 will now be readily understood. A sample to be studied or investigated is introduced into the eluent flow system at the injection valve 54 and thereupon proceeds into the packed capillary column 60 of the invention. The packed capillary column makes possible the use of a relatively small volume of eluent and also facilitates a marked reduction in rate of flow or throughput. The effluent from the liquid packed capillary column is detected and recorded in a manner well known in the art.

However, rather than terminating the analytical procedure at this stage, the eluent containing the species of interest is directed from the detector, through a switching valve 80 to the interface capillary tube or vaporizing chamber 100, housed within an oven 150. In the interface capillary tube or vaporizing conduit 100, the eluent is transformed into vapor, and the temperature is so controlled that the eluent vapor passes through the butt connector 110 and through the gas capillary column 120 while the species of interest are "retained" in the capillary column 120. With the major portion of the eluent vaporized and discharged, the temperature of the oven is then reset (raised) to vaporize the species of interest which thereupon migrate through the gas capillary column and are separated and spaced in accordance with known techniques.

Finally, the species of interest are detected at the detector 130 and then recorded.

It will be appreciated that the apparatus and method described obviates the undesirable interference and related problems which a relatively substantial quantity of eluent pose in conducting analyses of the type described. The overall result of the method and apparatus of the invention is to achieve low flow rates allowing the loading of entire portions of the liquid column effluent into the gas chromatograph. The utilization of the interface capillary tube or vaporizing chamber, permits a relatively large injection of liquid into the gas chromatography column without the usual adverse effects upon the resolution or peak shape of the components of interest.

An additional advantageous feature of the apparatus and method of the invention is that the packed capillary liquid chromatography apparatus acts effectively as a highly efficient clean-up or chemical class fractionation stage prior to the introduction of the sample into the gas chromatography equipment, thus significantly reducing sample preparation time for many applications. It has been effectively demonstrated that on-line multidimensional high resolution liquid chromatography-gas chromatography system of the invention is markedly superior to what is achievable using either liquid chromatography or gas chromatography alone. The techniques of the invention are particularly suited to the determination of trace levels of contaminants in extremely complex matrices. With the inclusion of valve actuators and auto samplers, the system of the invention becomes totally automated.

Details of the experimental procedure and the apparatus used are set forth in the paragraphs below.

EXPERIMENTAL

Liquid Chromatography

The liquid chromatography system used consisted of a Jasco Uvidec II detector equipped with a modified cell whose illuminated volume was calculated from the capillary diameter and the slit size. Wavelengths used were 254 nm for evaluation and 220 nm for sample analysis at 0.01 to 0.04 AUFS. Injections were made using a Valco model NI4W injection valve (Valco Inst., Houston, Tex., U.S.A.). Injection volumes varied between 60 and 200 nl. The solvent delivery system consisted of a Waters model M-45 pump equipped with a micro flow module, which allowed flow rates ranging from 1 $\mu$/min. to 10 $\mu$l/min. The recorder used was a Sargent model xkr at 10 mv full scale.

The chromatography columns were constructed of fused silica capillaries with internal diameters of 100 $\mu$m, 250 pm (Spectran Corp., Sturbridge, Mass., U.S.A.) and 320 $\mu$m ((Hewlett Packard Co., Avondale, Pa., U.S.A.). Column lengths ranged from 75 cm to 110 cm. The columns were packed at 6000 psi using a slurry technique.

Chromatographic supports used were Zorbax ODS, dp=7 $\mu$m (DuPont Inst., Wilmington, Del., U.S.A.). ODS-Hypersil, dp=5 $\mu$m (Shandon Southern Products, Ltd., Cheshire, England), and Spherisorb ODS, dp=10 $\mu$m (Phase Sep., Hauppauage, N.Y., U. S. A.).

Test mixtures used to evaluate the liquid chromatography system and to establish elution orders contained ammonium nitrate, phenol, methyl benzoate and acetophenone, prepared by dissolving about 100 mg of the organics and about 500 mg of ammonium nitrate, used as a marker to determine column void volumes, in 50 percent acetonitrile-water. The mobile phase used for evaluation purposes was 75 percent acetonitrile-water.

Gas Chromatography

The gas chromatography system consisted of a Hewlett Packard Model 5790 system equipped with a flame ionization detector.

Connection of the micro liquid chromatography equipment to the gas chromatography equipment was made with a switching valve 80 (Valco Model 4NI10WT) to keep the dead volume to a minimum. The valve was installed outside of the oven cabinet. An inlet section of capillary material free of stationary phase was connected between the switching valve 80 and the analytical column. This section, heretofore referred to as the vaporization conduit, interface capillary tube or the vaporizing chamber 100, as previously described, effectively focused the components of interest at the head of the gas chromatography column 120. A glass-lined stainless steel butt connector 110 (Scientific Glass Engineering, Inc., Austin, Tex., U.S.A.) was used to couple the interface capillary tube 100 to the analytical gas column 120 with essentially no "dead volume."

The analytical gas chromatography column used was a 30 meter, 0.25 mm I.D. column coated with Supelcowax 10 of 0.25 pm thickness (Supelco, Inc., Bellefonte, Pa., U.S.A.). The carrier gas was helium at a linear velocity of 68 cm/sec and nitrogen at 30 ml/min was used as the make-up gas for the flame ionization detector 130, operated at 265° C. The temperature of the oven 150 was maintained at 115° C. for 7 minutes, with a temperature program to 245° C. at 5° per minute.

A block diagram of the apparatus and its arrangement appears as FIG. 1.

RESULTS AND DISCUSSION

Effect and Role of Detector Cell Volume

The maximum detector cell volume for a packed capillary system that does not significantly contribute to system band broadening has been defined as:

$$Vd = 0.18\ Ldp\ dc$$

where L=column length, dp=particle size and dc=capillary diameter. For a 75 cm column of 250 $\mu$m I.D. packed with 7 $\mu$m particles, the maximum detector volume would be 27 nl.

Effect of Column Diameter

Although column efficiency does not appear to depend upon column diameter in packed systems, fluctuations in packing density which may occur over the column diameter and temperature gradients generated due to viscous friction may contribute to band broadening which can be minimized by decreasing the column diameter.

Effect of Particle Size Diameter

The theoretical limit in terms of plate height of a packed column chromatography system has been described as being equivalent to two times the particle diameter. In the work conducted and reported herein, the plate heights range from 2.6 times particle diameter (10 $\mu$m) to 3.4 times particle diameter (5 $\mu$m) at the lower linear velocities which were employed.

EXAMPLE

A sample of coal tar was analyzed by micro HPLC as described hereinabove using a mobile phase of 100 percent acetonitrile.

Figure 2:
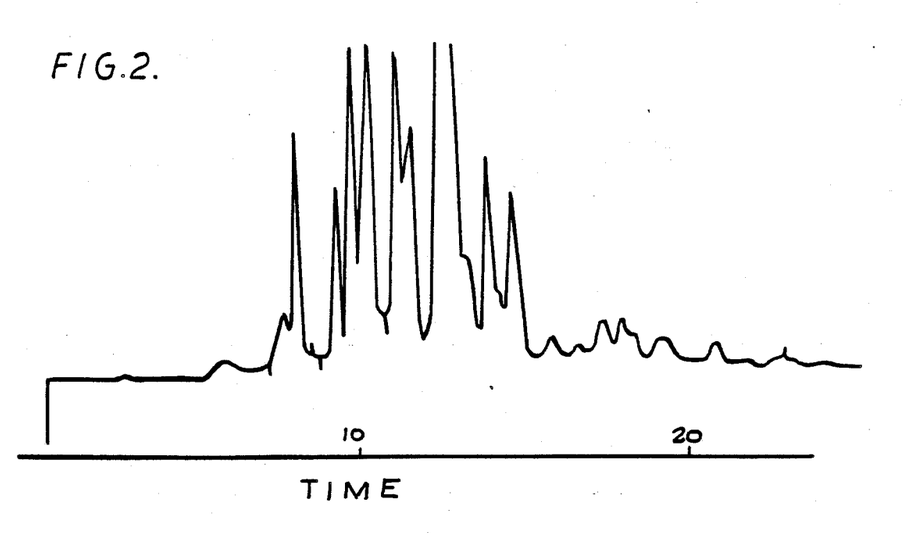
FIG. 2 is a chromatogram obtained in a conventional high performance liquid chromatographic system, including the type of resolution obtainable using a coal tar sample with 100 percent acetonitrile as the mobile phase.
Figure 3:
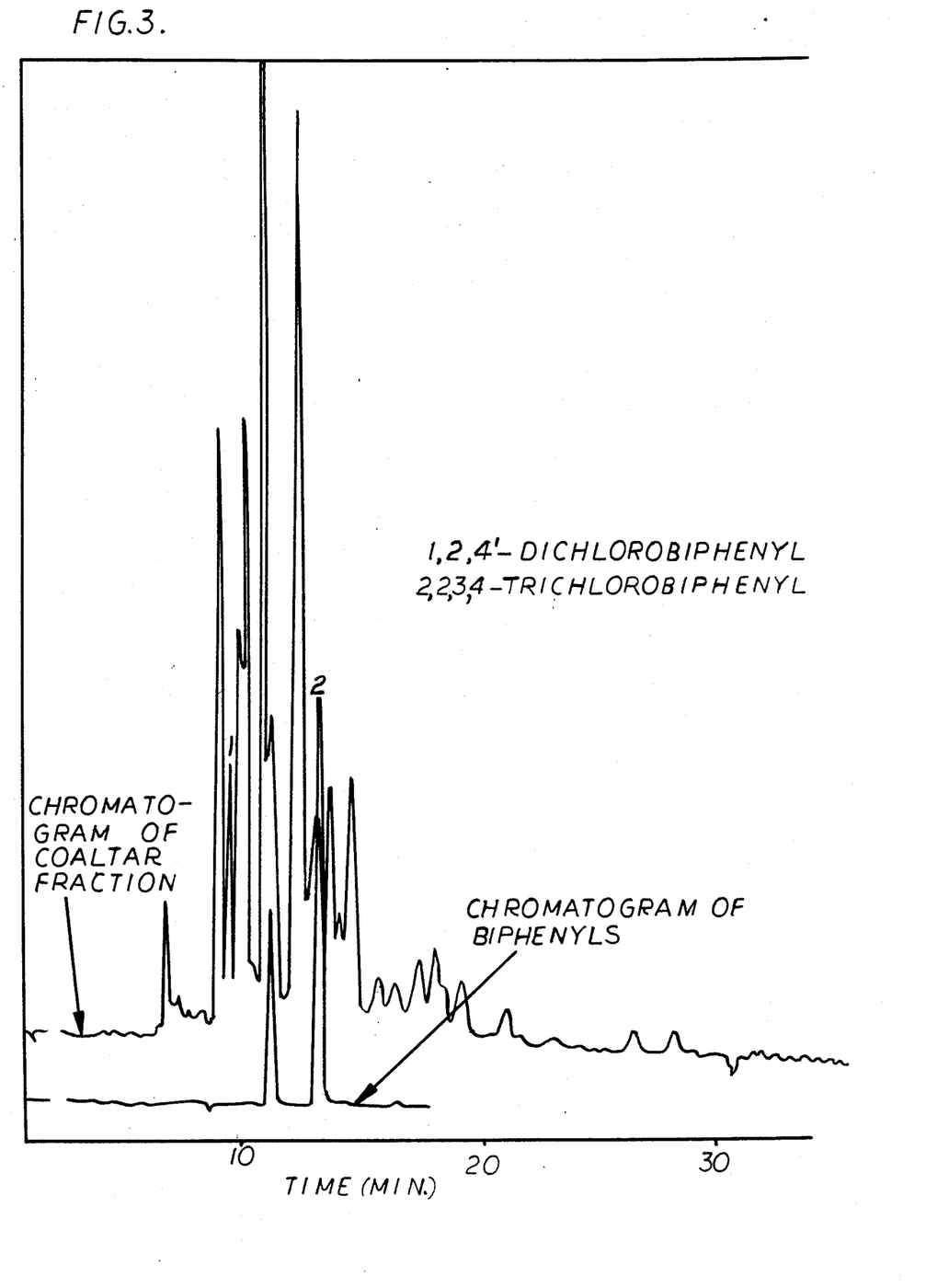
FIG. 3 is a chromatogram in which polychlorinated biphenyls have been elutriated with components of a coal tar mixture, and analyzed using the liquid chromatography apparatus and method of the present invention.

A chromatogram obtained utilizing a conventional HPLC system is included herein as FIG. 2. This chromatogram should be compared with that of FIG. 3 in which the system of the invention was employed.

Figure 4:
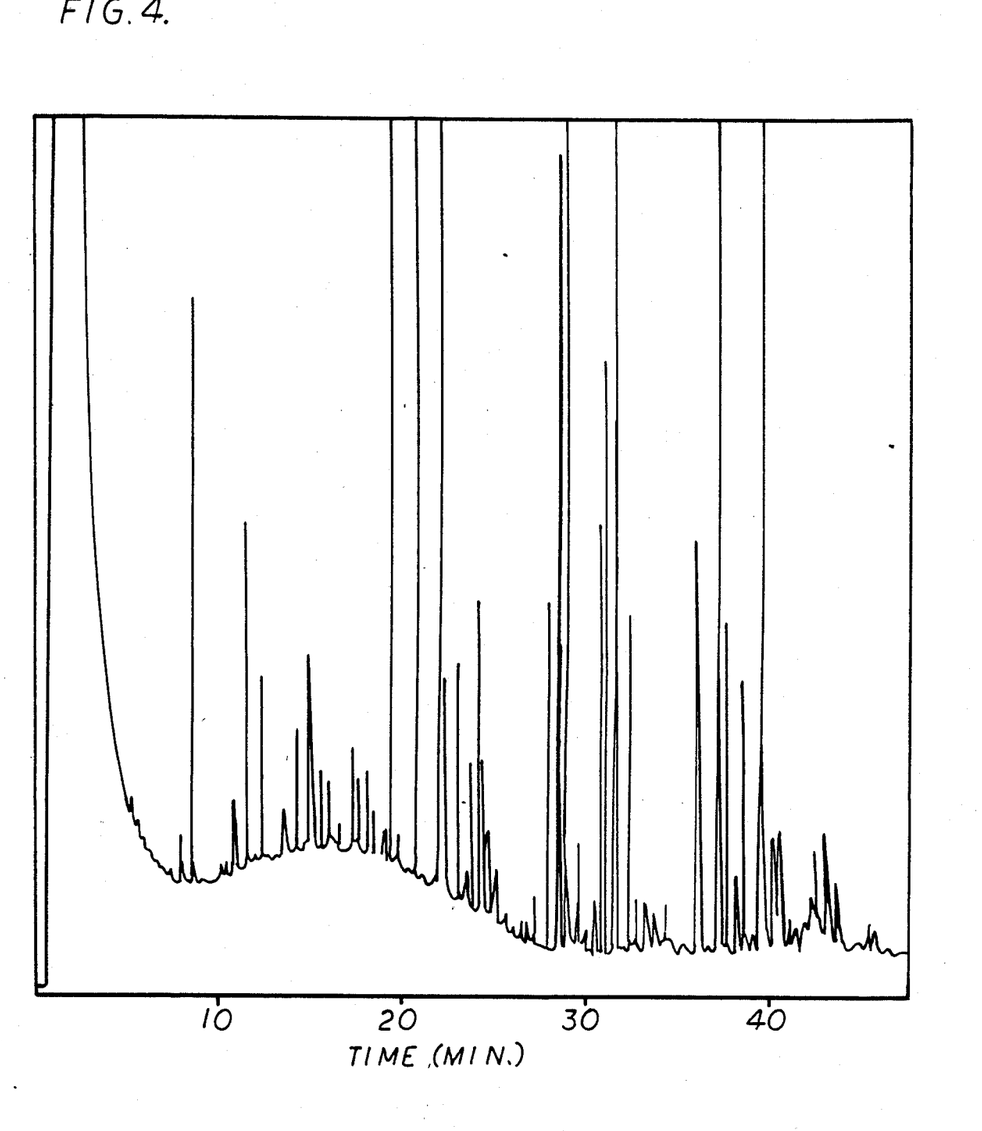
FIG. 4 represents a chromatogram obtained upon injection of a 10 microliter aliquot of a coal tar sample into the gas chromatograph port of the apparatus of the invention.
Figure 5:
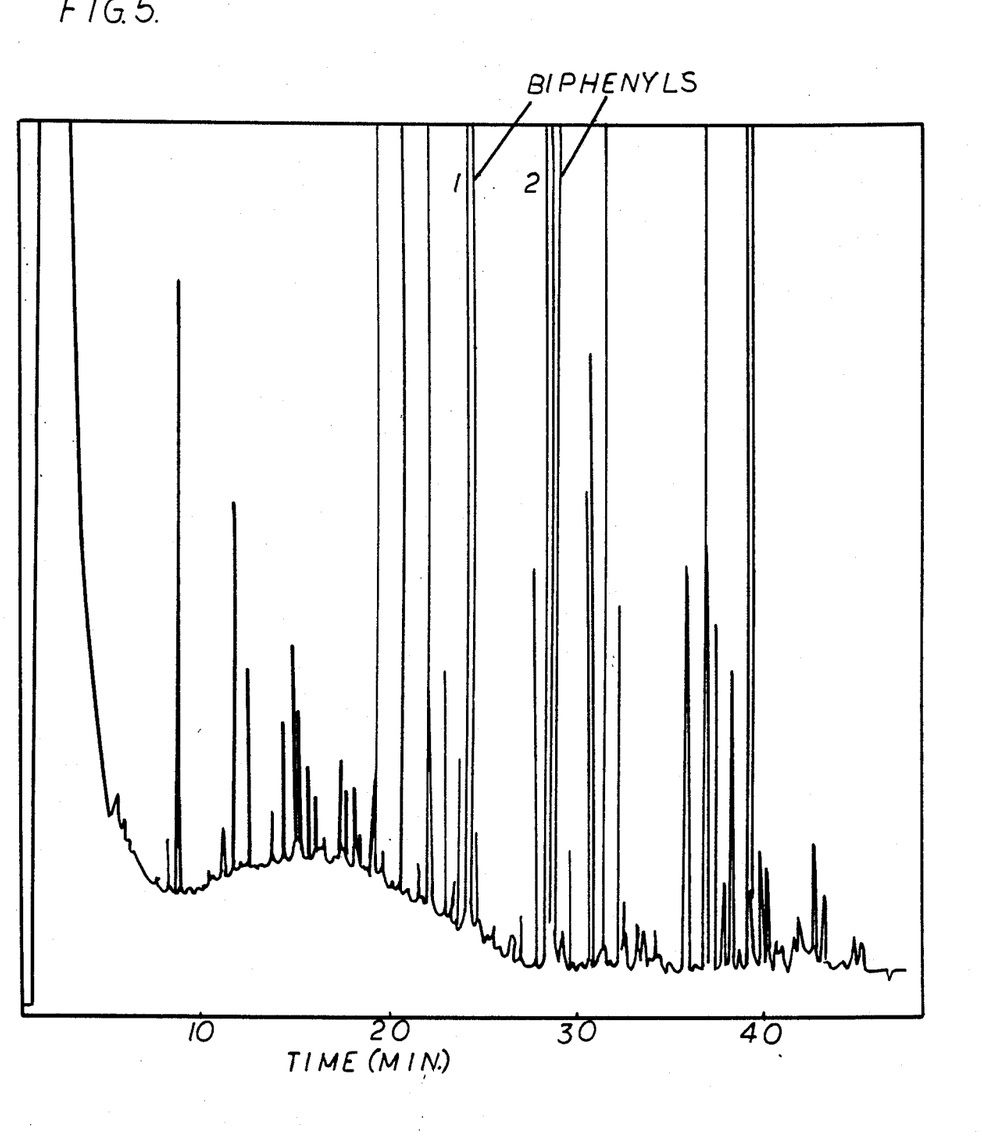
FIG. 5 is a chromatogram similar to that of FIG. 4 but of a sample which included polychlorinated biphenyls, and indicating that the polychlorinated biphenyls co-elute with various components of the coal tar mixture in the gas chromatography system.

A 10 $\mu$l injection of a coal tar sample and a coal tar sample containing the polychlorinated biphenyls (species of interest) produced the chromatograms depicted in FIGS. 4 and 5. As clearly indicated, the polychlorinated biphenyls elute with various components of the coal tar mixture in the gas chromatographic system.

Figure 6:
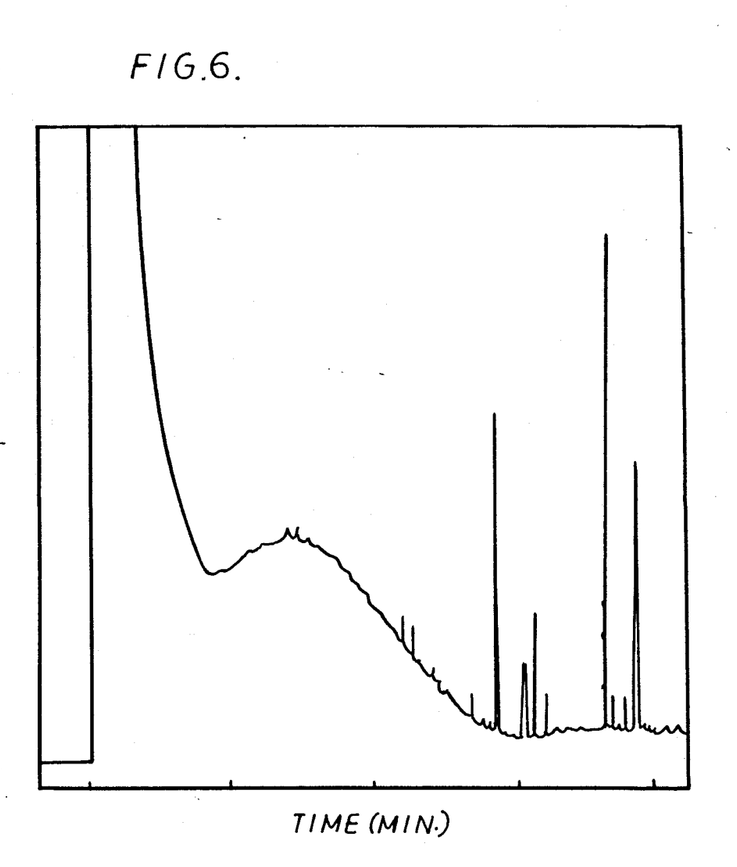
FIG. 6 is a chromatogram of a selected portion of the liquid chromatographic column effluent known to contain the components of interest and introduced into the gas chromatographic section of the apparatus of the invention.
Figure 7:
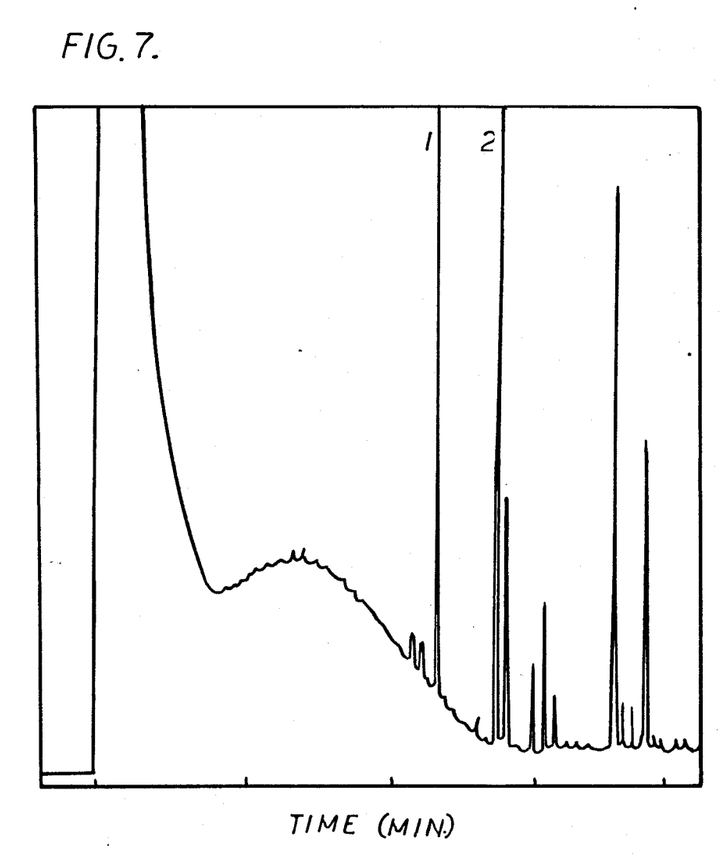
FIG. 7 is a chromatogram of the coal tar fraction shown in FIG. 6, but containing as well the polychlorinated biphenyls not included in chromatogram of FIG. 6.

The liquid chromatographic system was then connected to the switching valve 80 and the selected portion of the liquid chromatographic column effluent known to contain the components of interest was introduced into the gas chromatographic system. FIG. 6 represents a chromatogram using the combined liquid chromatographic and gas chromatographic system of the invention and carried out on a coal tar mixture that did not contain the polychlorinated biphenyls, while FIG. 7 represents a chromatogram of coal tar containing the polychlorinated biphenyls of interest.

The volume injected into the gas chromatography system was about 40 $\mu$l. The use of an interface capillary tube or vaporizing chamber, in accordance with the invention, allowed this quantity of polar eluent to be injected without any detrimental effects on the shapes of the peaks of interest. It is evident upon comparison of FIGS. 6 and 7 that the polychlorinated biphenyls of interest are effectively resolved from all other components in the coal tar matrix, indicating the superiority of the multidimensional approach of the invention to either liquid or to gas chromatography alone, and the superiority of the present invention over prior on-line combination systems.

It will be appreciated from the foregoing disclosure that there is herein provided a multi-dimensional chromatographic system for effectively coupling a packed capillary liquid chromatographic column to a capillary gas chromatographic column. The typical low flow rates of the micro liquid chromatographic system allows the loading of entire portions of the column effluent into the gas chromatographic system. The use of a vaporizing chamber or capillary tube allows injection of an increased volume of liquid without adverse effects upon the resolution or peak shape of the components of interest.

While a particular preferred embodiment of the invention has been shown and described, it will be obvious to those skilled in the art that changes and modifications may be made without departing from the invention in its broader aspects.

TERMS

Whenever used in the appended claims, the following terms are intended to be given the meaning as follows:

"Quantitative Transfer" means introduction of the total component(s) of interest in the mixture eluting from the liquid chromatography column to the gas chromatography column.

"Effective Operating Flow Rate" means a flow rate not greater than that which would not allow effective trapping of the component(s) of interest at the head of the gas chromatography column.

"Effective Trapping" means and is shown by not obtaining detrimental peak shapes, band broadening, or significantly diminished resolution which occurs because of excess eluent volume which carries the components(s) of interest from the interface into the gas chromatography column to an extent that it creates band broadening, diminished resolution, and/or detrimental peak shape shown by excessive nongaussian peak character.

"Detrimental Peak Shape", "Band Broadening", and "Diminished Resolution" mean those conditions which produce unnecessary merged peaks, unnecessary nongaussian shapes of peaks which are difficult to quantitate, or peaks that are unnecessarily broadened to the point that quantitation at lower levels based, e.g., on peak height, becomes difficult or impossible.

"Low Flow Rate Liquid Chromatography Column" means a column whose effective operating flow rate allows quantitative transfer of the component(s) of interest into a gas chromatography column through a capillary interface. Low flow rate liquid chromatography columns useful in the invention are generally capillary columns of an inner diameter of about 1 mm or less. Under careful flow conditions it is contemplated that larger columns can be employed for the purposes of the invention, e.g., liquid chromatography columns having an inner diameter of generally about 2 mm or less.

What is claimed is:

1. A method for conducting on-line chromatographic analysis of a sample aliquot containing organic species of interest and employing an analytical system including, in combination, a liquid chromatography column and a gas chromatography column, a heater for said gas chromatography column, and detection and display apparatus for providing visual inidcia of species of interest present in a sample aliquot to be analyzed, said method including the steps of:
  rendering the liquid chromatography column, a packed or wall-coated capillary column, physically arranging the packed or wall-coated capillary liquid chromatographic column and the gas chromatographic column in an in-line communication configuration;
  connecting in inter-fluid flow communication with an interposing between said fluid chromatography column and said gas chromatography column, an interface capillary tube chamber for receiving a liquid effluent from the liquid chromatography column;
  adding to the interface capillary tube eluent contained in the liquid effluent received from the liquid chromatographic column and simultaneously vaporizing the eluent to convert the eluent to a gas and to free species of interest present in the eluent;
  vaporizing the species of interest, and
  delivering the species to the gas chromatography column to effect separation thereof for detection and recordation.

2. A method for conducting coupled and on-line liquid and gas chromatographic analysis of sample comprising:
  adding sample to a liquid mobile phase and eluting the mixture through a low flow rate liquid chromatography column to resolve a component of interest which emerges from the liquid chromatography column as a sample band;
  quantitatively transferring the effluent of the column containing the band of interest into an interface capillary tube and simultaneously maintaining the tube at a temperature to vaporize the mobile phase;
  quantitatively transferring the sample band from the interface into a gas chromatography column which is relatively nonretentive of the mobile phase but retains the band of interest whereby said band is reconcentrated at the head of the gas chromatography column;
  eluting the previously reconcentrated band of interest through the gas chromatography column by using a gaseous mobile phase and effective temperature increase which will allow further resolution of the band of interest; and
  detecting the band of interest eluting from the gas chromatography column.

3. The method of claim 2 wherein the method is practiced to resolve and detect plural components of interest.

4. The method of claim 2 wherein the low flow rate liquid chromatography column comprises a capillary column of about 1 mm or less.

5. A method of conducting coupled liquid and gas chromatography analysis wherein the method uses a liquid chromatography column, a retention gap, and a gas chromatography column arranged in series, the method comprising:
  eluting sample solute dispersed in liquid solvent through the liquid chromatography column;
  introducing the solvent from the liquid chromatography column into the retention gap while the retention gap is heated to a temperature at which the solvent reaches its boiling point, thereby vaporizing the solvent and passing the vaporized solvent out of the retention gap while simultaneously introducing the solvent into the retention gap; thereafter introducing carrier gas into the retention gap and passing the carrier gas through said retention gap and gas chromatography column to elute the sample solute; and detecting the sample solute in the effluent of the gas chromatography column.

6. The method of claim 5 wherein the liquid chromatography column is a low flow rate liquid chromatography column.

* * * * *